(12) United States Patent
Zhou et al.

(10) Patent No.: US 9,788,769 B2
(45) Date of Patent: Oct. 17, 2017

(54) HANDHELD MULTI-PARAMETER MEASURING INSTRUMENT

(71) Applicant: SHENZHEN VIATOM TECHNOLOGY CO., LTD., Guangdong (CN)

(72) Inventors: Saixin Zhou, Guangdong (CN); Bing Wang, Guangdong (CN); Pinbo Wang, Guangdong (CN)

(73) Assignee: SHENZHEN VIATOM TECHNOLOGY CO., LTD., Guangdong (CN)

( * ) Notice: Subject to any disclaimer, the term of this patent is extended or adjusted under 35 U.S.C. 154(b) by 109 days.

(21) Appl. No.: 14/598,524

(22) Filed: Jan. 16, 2015

(65) Prior Publication Data

US 2015/0201876 A1    Jul. 23, 2015

(30) Foreign Application Priority Data

Jan. 17, 2014  (CN) .......................... 2014 1 0023954

(51) Int. Cl.
*A61B 5/1455*    (2006.01)
*A61B 5/024*    (2006.01)
(Continued)

(52) U.S. Cl.
CPC ........ *A61B 5/14552* (2013.01); *A61B 5/0261* (2013.01); *A61B 5/02416* (2013.01);
(Continued)

(58) Field of Classification Search
CPC ............ A61B 5/14551; A61B 5/02416; A61B 5/14552; A61B 5/7207; A61B 5/4818
See application file for complete search history.

(56) References Cited

U.S. PATENT DOCUMENTS 5,438,986 A * 8/1995 Disch ................. A61B 5/02422
                                                    600/310
2006/0133052 A1* 6/2006 Harmon ................ G06F 1/1616
                                                    361/752
(Continued)

FOREIGN PATENT DOCUMENTS

| CN | 1830382 A | 9/2006 | |
|---|---|---|---|
| CN | 103479342 A | 1/2014 | |
| TW | EP 1693002 A1 * | 8/2006 | ........... A61B 5/0404 |

OTHER PUBLICATIONS

Office Action dated Mar. 30, 2015 issued in correspondence Chinese Patent Application No. 2015032501164950, pp. 1-7.
(Continued)

*Primary Examiner* — Eric Winakur
*Assistant Examiner* — Marjan Fardanesh
(74) *Attorney, Agent, or Firm* — Polsinelli PC (57) ABSTRACT

A handheld multi-parameter measuring instrument includes: a housing having a sidewall and opposed first and second surfaces, the sidewall, the first surface and the second surface cooperatively forming a cavity; a cover attached to the sidewall and rotatably connected to the housing; the blood oxygen transducer includes a light emitting unit and a light receiving unit; the light emitting unit is configured to emit red light and infrared light alternately; the light receiving unit is configured to receive the red light and the infrared light emitted from the light emitting unit; the signal processing unit is received in the cavity of the housing and is configured to control the light emitting unit to emit the red light and the infrared light alternately; the signal processing unit is further configured to calculate oxygen saturation based on a signal received by the light receiving unit; the light emitting unit is located at a side of the cover attached to the housing, and the light receiving unit is located at the sidewall. When measuring blood oxygen saturation, one
(Continued)

hand holds the first surface and the second surface of the housing, and one finger of the hand is inserted between the cover and the sidewall of the housing attached to the cover. This handheld multi-parameter measuring instrument is easy to use and has a high measuring accuracy.

15 Claims, 7 Drawing Sheets

(51) Int. Cl.
    *A61B 5/026*     (2006.01)
    *A61B 5/00*     (2006.01)
    *A61B 5/0404*     (2006.01)

(52) U.S. Cl.
    CPC .......... *A61B 5/0404* (2013.01); *A61B 5/7278* (2013.01); *A61B 5/742* (2013.01); *A61B 2560/0431* (2013.01)

(56) References Cited

U.S. PATENT DOCUMENTS

| | | | | |
|---|---|---|---|---|
| 2008/0306395 | A1* | 12/2008 | Xu ..................... | A61B 5/02416 600/509 |
| 2009/0137891 | A1* | 5/2009 | Wang ................... | A61B 5/0404 600/384 |
| 2010/0240972 | A1* | 9/2010 | Neal ................... | A61B 5/14552 600/324 |
| 2011/0286641 | A1* | 11/2011 | Schneider .......... | G06K 9/00046 382/124 |
| 2014/0114199 | A1* | 4/2014 | Lamego ............... | A61B 5/6838 600/479 |

OTHER PUBLICATIONS

Office Action dated Nov. 23, 2015 in corresponding Chinese Patent Application No. 2015111801469940, pp. 1-7.

* cited by examiner

FIG. 7

HANDHELD MULTI-PARAMETER MEASURING INSTRUMENT

CROSS-REFERENCE TO RELATED APPLICATIONS

This application claims priority to Chinese Patent Application Serial No. 201410023954.4 filed on Jan. 17, 2014 the entire contents of which is hereby incorporated by reference in its entirety.

FIELD OF THE INVENTION

The present disclosure relates to medical devices, and more particularly relates to a handheld multi-parameter measuring instrument.

BACKGROUND OF THE INVENTION

Multi-parameter measuring instrument usually includes a plurality of sensors, so as to perform multiply measurements of physiological parameters, such as electrocardiogram (ECG), body temperature, blood sugar, blood pressure, blood oxygen saturation, pulse rate, perfusion strength, or the like. Among them, the blood oxygen saturation, the pulse rate, and the perfusion strength can be measured by a blood oxygen transducer, while vital information such as the ECG, heart rate, etc can be measured by an ECG sensor.

Since the users of multi-parameter measuring instrument are mostly non-professional home users with self-testing using method, and at least two sensors are integrated, in order to ensure ease of use and ease of maintenance of the product, the integrated approach and distribution of multiple sensors are particularly important. However, the integrated approach of the blood oxygen transducer of the conventional multi-parameter measuring instrument is inappropriate and inconvenient, or although it is easy to use, there is a problem of poor measurement accuracy.

SUMMARY OF THE INVENTION

Accordingly, it is necessary to provide a handheld multi-parameter measuring instrument suitable for home use and having a high measuring precision.

A handheld multi-parameter measuring instrument includes:

a housing having a sidewall and opposed first and second surfaces, the sidewall, the first surface and the second surface cooperatively forming a cavity;

a cover attached to the sidewall and rotatably connected to the housing, a finger being capable of being received between the cover and the sidewall of the housing attached to the cover; and a blood oxygen measuring device including a blood oxygen transducer and a signal processing unit, the blood oxygen transducer comprising a light emitting unit and a light receiving unit; the light emitting unit being configured to emit red light and infrared light alternately; the light receiving unit being configured to receive the red light and the infrared light emitted from the light emitting unit; wherein the signal processing unit is received in the cavity of the housing and is configured to control the light emitting unit to emit the red light and the infrared light alternately; the signal processing unit is further configured to calculate oxygen saturation based on a signal received by the light receiving unit;

wherein the light emitting unit is located at a side of the cover attached to the housing, and the light receiving unit is located at the sidewall of the housing attached to the cover;

or the light emitting unit is located at the sidewall facing the cover, and the light receiving unit is located at a side of the cover facing the housing;

or the light emitting unit and the light receiving unit are both located at the sidewall facing the cover;

when measuring blood oxygen saturation, one hand holds the first surface and the second surface of the housing, and one finger of the hand is inserted between the cover and the sidewall of the housing attached to the cover.

In one embodiment, the blood oxygen measuring device further includes:

an optoelectronic interface unit, by which the light emitting unit and the light receiving unit are electrically coupled to the signal processing unit;

a memory unit received in the cavity and electrically coupled to the signal processing unit, the memory unit being configured to store the oxygen saturation calculated by the signal processing unit; and a display unit located at the housing, the display unit being electrically coupled to the signal processing unit and configured to display the oxygen saturation calculated by the signal processing unit.

In one embodiment, the signal processing unit is further configured to calculate at least one of pulse rate, perfusion strength, and pulse waveform based on the signal received by the light receiving unit.

In one embodiment, the cover and the sidewall of the housing attached to the cover form a buffer chamber therebetween.

In one embodiment, the housing has a rectangular shape, when a right hand of a user holds the first surface and the second surface, the first surface faces the user, the cover is located at a upper right of the housing, and the cover is attached to a sidewall at the corner of the housing or a sidewall at the top of the housing.

In one embodiment, the cover and the sidewall of the housing attached to the cover form a buffer chamber therebetween, and the buffer chamber is formed by depressing inward of sidewall of the housing attached to the cover.

In one embodiment, the cover is attached to the sidewall located at the corner of the housing, and the cover and the sidewall of the housing attached to the cover form the buffer chamber therebetween; the cover is a curved plate, the sidewall of the housing attached to the cover has an arcuate shape, the buffer chamber is formed by the cover and the sidewall of the housing attached to the cover cooperatively.

In one embodiment, a curvature of the outer surface of the cover is the same as a curvature direction of the sidewall of the housing attached to the cover; a bending direction of the outer surface of the cover is the same as a bending direction of the sidewall of the housing attached to the cover, and a center of a circle of the outer surface of the cover is located inside the housing.

In one embodiment, the handheld multi-parameter measuring instrument further includes limiting means located at the housing configured to limit a maximum rotating angle of the cover with respect to the housing, the maximum rotating angle ranging from 15 degrees to 75 degrees.

In one embodiment, the cover and the sidewall of the housing attached to the cover form a buffer chamber therebetween, and the buffer chamber is formed by depressing inward of sidewall of the housing attached to the cover.

In one embodiment, the cover is attached to the sidewall located at the corner of the housing, and the cover and the sidewall of the housing attached to the cover form the buffer chamber therebetween; the cover is a curved plate, the sidewall of the housing attached to the cover has an arcuate shape, the buffer chamber is formed by the cover and the sidewall of the housing attached to the cover cooperatively.

In one embodiment, a bending direction of the inner surface of the cover is the same as a bending direction of the sidewall of the housing attached to the cover, and a center of a circle of the inner surface of the cover is located inside the housing;

a curvature of the outer surface of the cover is the same as a curvature direction of the sidewall of the housing attached to the cover; a bending direction of the outer surface of the cover is the same as a bending direction of the sidewall of the housing attached to the cover, and a center of a circle of the outer surface of the cover is located inside the housing.

In one embodiment, the handheld multi-parameter measuring instrument further includes limiting means located at the housing configured to limit a maximum rotating angle of the cover with respect to the housing, the maximum rotating angle ranging from 15 degrees to 75 degrees.

In one embodiment, the limiting means is a blocking structure located at the sidewall of the housing attached to the cover, the blocking structure is located at a end of the cover connected to the housing, such that the end of the cover connected to the housing is stopped by the blocking structure when the cover rotates to a certain angle, thereby preventing the cover from further rotating.

In one embodiment, the handheld multi-parameter measuring instrument further includes restoring means configured to attach the cover to the sidewall of the housing.

In one embodiment, the restoring means is a magnetic mechanism; the magnetic mechanism comprises two magnetic elements, which are located at a side of the cover attached to the housing and the sidewall of the housing attached to the cover, respectively, the two magnetic elements are attracted to each other;

or the magnetic mechanism comprises a magnetic element and a metal sheet, one of the magnetic element and the metal sheet is located at a side of the cover attached to the housing, the other one is located at the sidewall of the housing attached to the cover, the magnetic element is attracted to the metal sheet.

In one embodiment, the cover is rotatably connected to the housing via a rotating shaft, the restoring means is a torsion spring coiled on the rotating shaft.

In one embodiment, a finger inserting recess is provided between an end of the cover away from the housing and the sidewall, thereby the finger is capable of inserting the finger inserting recess to open the cover attached to the housing.

When using the handheld multi-parameter measuring instrument to measure the blood oxygen saturation, one hand of the user can hold the first surface and the second surface of the housing, and the finger of the hand can be place between the cover and the housing. The signal processing unit controls the light emitting unit to emit the red light and the infrared light alternately, which go through the finger or are reflected by the finger, and then transmitted to the light receiving unit. The signal processing unit then calculates the oxygen saturation based on a signal received by the light receiving unit.

In the forgoing handheld multi-parameter measuring instrument, the cover is disposed on the sidewall of the housing, and the blood oxygen transducer is integrated on the housing, therefore there is no need to employ cable, connector or the like, the instrument has the features of easy to use, easy to maintain, low cost, high accuracy, and good resistance to ambient light interference. When the light emitting unit and the light receiving unit are located at the same side, the cover can effectively prevent the interference of ambient light, thereby enhancing the accuracy and repeatability of blood oxygen transducer. The cover can also protect the light emitting unit and the light receiving unit from contamination and abrasion, which can affect the light transmittance, thereby further enhancing the accuracy and repeatability of blood oxygen transducer. When the light emitting unit and the light receiving unit are located at opposite sides, the handheld multi-parameter measuring instrument can have a better measuring accuracy comparing to the reflective-type blood oxygen transducer. The handheld multi-parameter measurement instrument is easy to use, easy to maintain, very suitable for non-professional home self-test use. In addition, since the cover is disposed on the sidewall of the housing, there will be more space in the housing for integrating other sensors.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Referring to FIGS. 1 to 4, an embodiment of a handheld multi-parameter measuring instrument 10 includes a housing 100, a cover 200, a blood oxygen measuring device 300, a limiting means 400, and a restoring means 500.

The housing 100 has a sidewall 110 and opposed first and second surfaces 120, 130. The sidewall 110, the first surface 120, and the second surface 130 cooperatively form a cavity 140. The cover 200 is attached to the sidewall 110 of the housing 100 and is rotatably connected to the housing 100, such that a finger 22 can be received between the cover 200 and the sidewall 110 of the housing 100 attached to the cover 200. In the illustrated embodiment, the cover 200 is rotatably connected to the housing 100 via a shaft 210.

Referring to FIGS. 1 to 5, in the illustrated embodiment, the housing 100 has a substantially rectangular shape. When a right hand 20 of a user hold the first and second surfaces 120, 130 of the housing 100, the first surface 120 faces the user, and the cover 200 is located at an upper right of the housing 100, i.e., the cover 200 is attached to a sidewall 110 of the housing 100 at a corner. The sidewall 110 of the housing attached to the cover 200 has an arcuate shape. When measuring blood oxygen saturation, the handheld multi-parameter measuring instrument 10 is held by other fingers except the finger 22 to be measured, which is inserted between the cover 200 and the sidewall 110 of the housing 100 attached to the cover 200.

Figure 6:
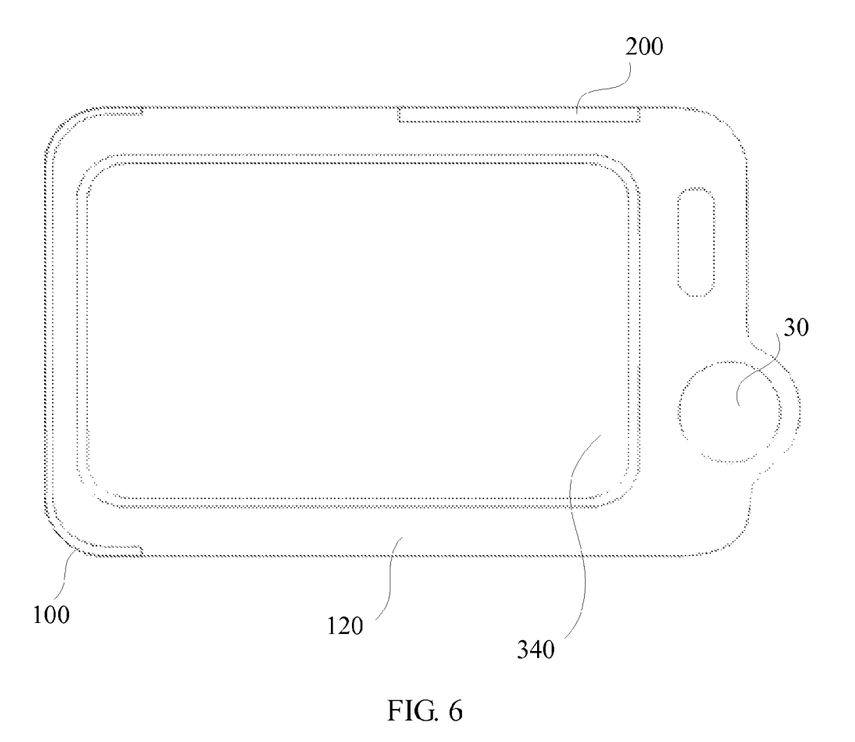
FIG. 6 is a front view of a handheld multi-parameter measuring instrument according to another embodiment.
Figure 7:
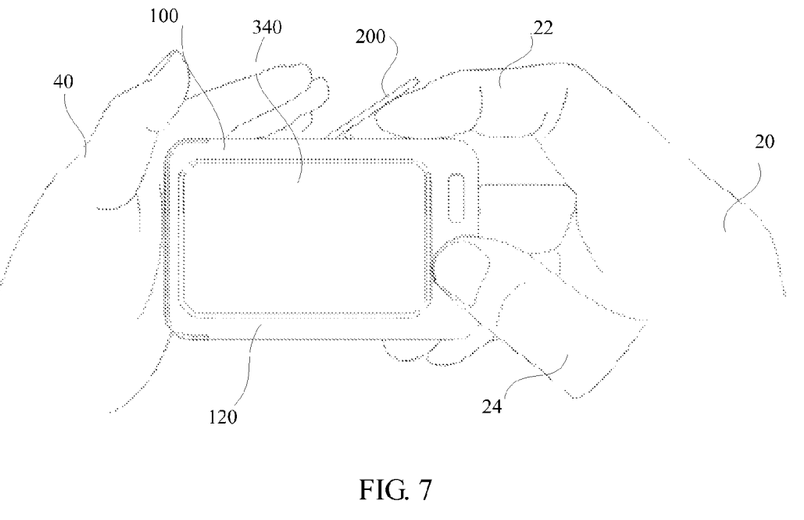
FIG. 7 is a front view of the handheld multi-parameter measuring instrument integrated with the blood oxygen transducer of FIG. 6 in a working state.

Referring to FIGS. 6 and 7, in alternative embodiments, the cover 200 can be attached to a sidewall at the top of the housing 100, and the sidewall of the housing 100 attached to the cover 200 is planar. It is to be understood that, the housing 100 may have other shapes, such as cylindrical or the like. When the housing 100 is shaped as a cylinder, the first and the second surfaces 120, 130 are both round surfaces.

Furthermore, a buffer chamber can be formed between the cover 200 and the sidewall 110 of the housing 100 attached to the cover 200. When subjected to external force or impacts, the buffer chamber can protect the blood oxygen measuring device 300 from being damaged. It is to be understood that, the buffer chamber can be omitted.

In the present embodiment, the cover 200 is a curved plate, the sidewall 110 of the housing 100 attached to the cover 200 has an arcuate shape, the buffer chamber is formed by the cover 200 and the sidewall 110 of the housing 100 attached to the cover 200 cooperatively. The arcuate shape of the sidewall 110 can help the end of the finger 22 to be measured attach to the housing 100, which allows the user to measure the oxygen saturation in a more comfortable state. In addition, when the cover 200 is attached to the sidewall of the housing at the corner, and the sidewall 110 of the housing 100 attached to the cover 200 has the arcuate shape, it can be ensured that under the premise of a small size, the handheld multi-parameter measuring instrument 10 can obtain the largest space to receive the finger 22 to be measured, such that the size of the instrument 10 can be miniaturized while maintaining a accurate measurement. Furthermore, the arcuate shaped surface can form a good contact and shelter to the finger 22, which can further reduce the interference of ambient light.

In the illustrated embodiment, a bending direction of the inner surface of the cover 200 is the same as a bending direction of the sidewall 110 of the housing 100 attached to the cover 200, and a center of a circle of the inner surface of the cover 200 is located inside the housing 100. In addition, a curvature of the outer surface of the cover 200 is the same as a curvature direction of the sidewall 110 of the housing 100 attached to the cover 200. A bending direction of the outer surface of the cover 200 is the same as a bending direction of the sidewall 110 of the housing 100 attached to the cover 200, and a center of a circle of the outer surface of the cover 200 is located inside the housing 100. This kind of configuration can ensure a better appearance of the handheld multi-parameter measuring instrument 10, and a close protection can be formed to the blood oxygen measuring device 300.

It is to be understood that, in alternative embodiments, the cover 200 and the sidewall 110 of the housing 100 attached to the cover 200 form a buffer chamber therebetween, and the buffer chamber is formed by depressing inward of the sidewall 110 of housing 100 attached to the cover 200.

In the illustrated embodiment, in order to ensure a better appearance of the handheld multi-parameter measuring instrument 10, the sidewalls at the other three corners of the housing 100 also have arcuate shapes. All the four corners of the housing 100 being arcuate can make sure that the user is not easy to be scratched by the housing 100.

Figure 5:
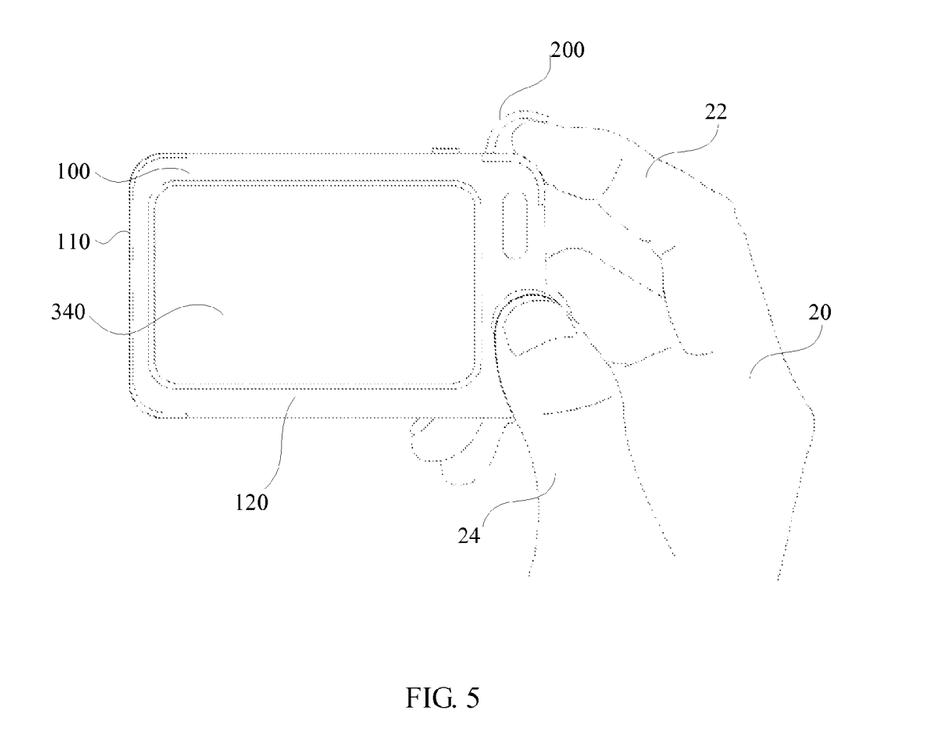
FIG. 5 is a front view of the handheld multi-parameter measuring instrument integrated with the blood oxygen transducer of FIG. 1 in a working state.

Referring to FIG. 5, in the illustrated embodiment, when using the handheld multi-parameter measuring instrument 10 to measure the blood oxygen saturation, one hand 20 of the user can hold the first surface 120 and the second surface 130 of the housing 100, and the finger 22 to be measured can be inserted between the cover 200 and the sidewall 110 of the housing 100 attached to the cover 200. In the illustrated embodiment, the finger 22 to be measured is the index finger, alternatively, it can be a middle finger, etc.

Figure 4:
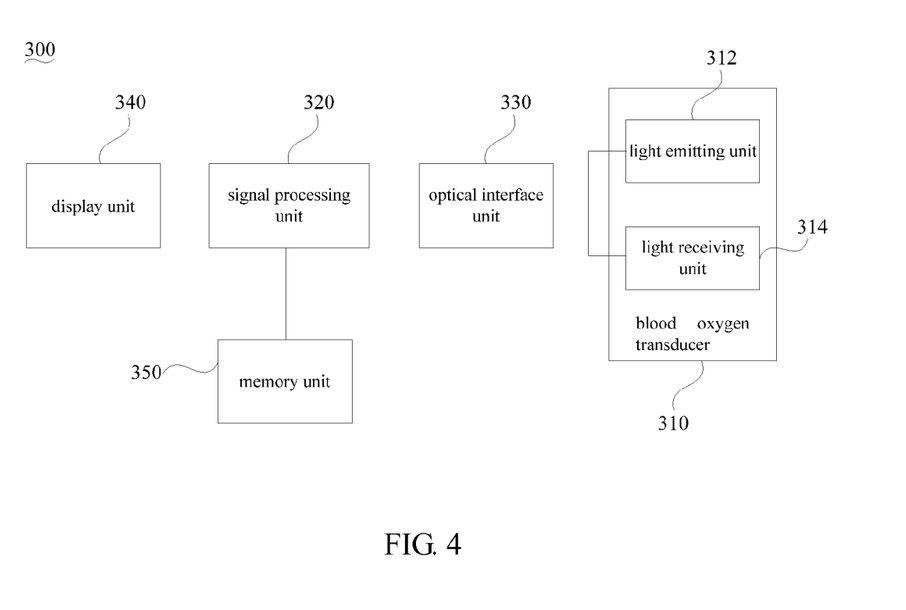
FIG. 4 is a block diagram of the blood oxygen measuring device of FIG. 1.

The blood oxygen measuring device 300 includes a blood oxygen transducer 310, a signal processing unit 320, an optoelectronic interface unit 330, a memory unit 350, and a display unit 340.

Figure 1:
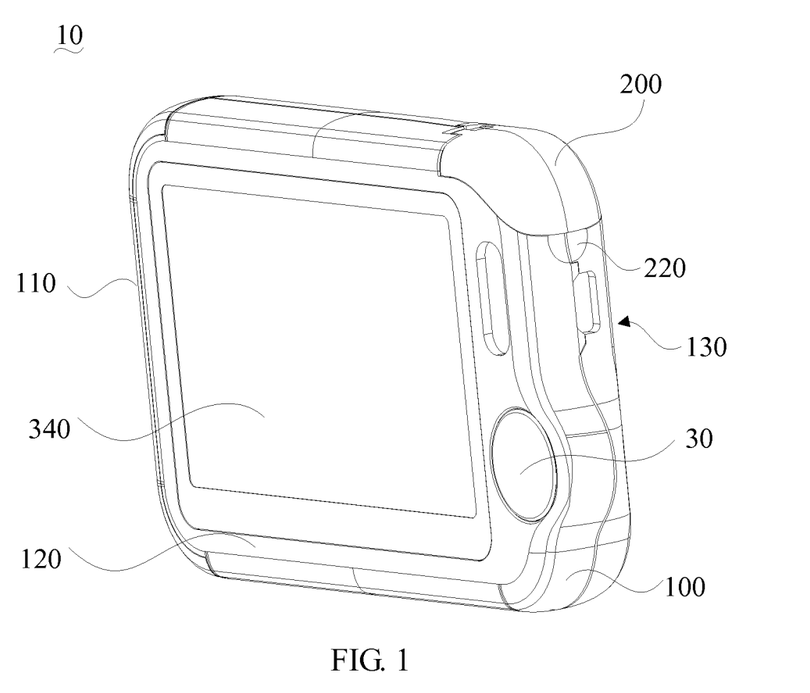
FIG. 1 is a perspective view of a handheld multi-parameter measuring instrument according to one embodiment.
Figure 2:
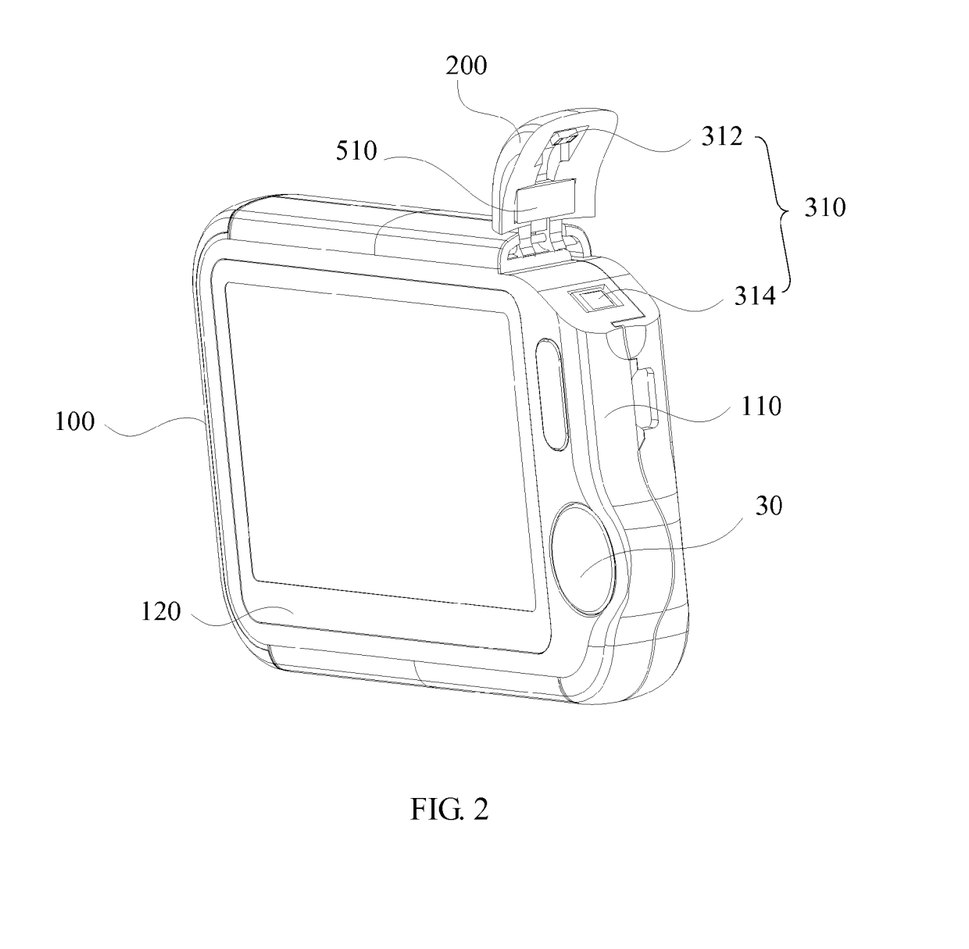
FIG. 2 is similar to FIG. 1, but showing the cover in a opened state.
Figure 3:
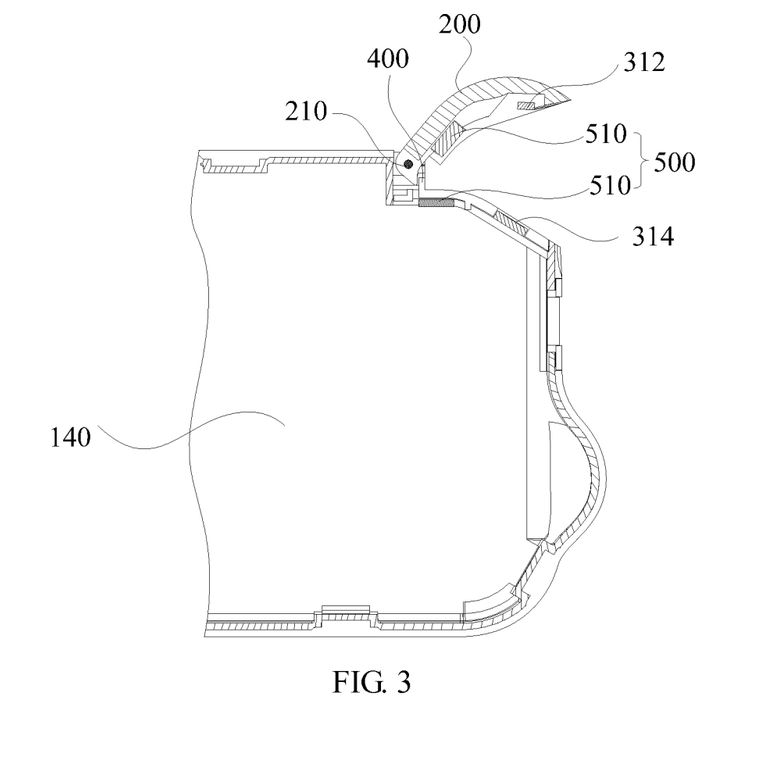
FIG. 3 is a partial cross-sectional view of the handheld multi-parameter measuring instrument integrated with the blood oxygen transducer of FIG. 1.

The blood oxygen transducer 310 includes a light emitting unit 312 and a light receiving unit 314. The light emitting unit 312 is configured to emit red light and infrared light alternately. The light receiving unit 314 is configured to receive the red light and the infrared light emitted from the light emitting unit 312. In the illustrated embodiment, the light emitting unit 312 is located at a side of the cover 200 attached to the housing 100, and the light receiving unit 314 is located at the sidewall 110 of the housing 100 attached to the cover 200. It is to be understood that, in alternative embodiments, the light receiving unit 314 can be located at a side of the cover 200 attached to the housing 100, and the light emitting unit 312 can be located at the sidewall 110 of the housing 100 attached to the cover 200. Alternatively, the light emitting unit 312 and the light receiving unit 314 can both be located at the sidewall 110 of the housing 100 attached to the cover 200.

When the light emitting unit 312 and the light receiving unit 314 are located at the same side, the measuring principle of blood oxygen transducer 310 can be reflective-type. The cover 200 can effectively prevent the interference of ambient light, thereby enhancing the accuracy and repeatability of blood oxygen transducer 310. The cover 200 can also protect the light emitting unit 312 and the light receiving unit 314 from contamination and abrasion, which can affect the light transmittance, thereby further enhancing the accuracy and repeatability of blood oxygen transducer 310.

When the light emitting unit 312 and the light receiving unit 314 are located at opposite sides, the measuring principle of blood oxygen transducer 310 can be transmissive-type. The transmissive-type blood oxygen transducer 310 can have a better measuring accuracy comparing to that of the reflective-type.

The signal processing unit 320 is received in the cavity 140 of the housing 100. The signal processing unit 320 is configured to control the light emitting unit 312 to emit the red light and the infrared light alternately. The signal processing unit 320 is further configured to calculate the oxygen saturation based on a signal received by the light receiving unit 314. In the illustrated embodiment, the signal processing unit 320 is further configured to calculate at least one of pulse rate, perfusion strength, and pulse waveform based on the signal received by the light receiving unit 314.

The light emitting unit 312 and the light receiving unit 314 are electrically coupled to the signal processing unit 320 via the optoelectronic interface unit 330. The surfaces of the light emitting unit 312 and the light receiving unit 314 are packaged by OCA (Optically Clear Adhesive) for protection.

The memory unit 350 is received in the cavity 140 of the housing 100 and is electrically coupled to the signal processing unit 320. The memory unit 350 is configured to store the oxygen saturation as well as the pulse rate, perfusion strength, and pulse waveform, calculated by the signal processing unit 320.

The display unit 340 is located at the housing 100 and is electrically coupled to the signal processing unit 320. The display unit 340 is configured to display the oxygen saturation calculated by the signal processing unit 320. In the illustrated embodiment, the display unit 340 is located at the first surface 120 of the housing 100. The display unit 340 can also be configured to display at least one of the pulse rate, perfusion strength, and pulse waveform.

In the illustrated embodiment, the handheld multi-parameter measuring instrument 10 is further integrated with at least one of electrocardiogram (ECG) sensor, glucose sensor, and a temperature sensor. Referring to FIG. 7, taking ECG sensor for example, a first ECG electrode 30 (having a round shape) of the ECG sensor can be located at a side of the display unit 340, and a second ECG electrode (having a strip-like shape) of the ECG sensor can be located at the sidewall 110 opposite to the first ECG electrode 30, and an ECG measuring circuit can be received in the cavity 140 of the housing 100. The first ECG electrode, the ECG measuring circuit, the second ECG electrode, and the user can form a loop to implement the ECG measuring. When measuring the blood oxygen saturation and the ECG, the index finger 22 is inserted between the cover 200 and the housing 100, the thumb 24 presses the first ECG electrode 30, and the second ECG electrode is in contact with a palm of the other hand of the user or the skin of chest or ankle of the user.

In the illustrated embodiment, the limiting means 400 is located on the housing 100 to limit a maximum rotating angle of the cover 200 with respect to the housing 100. Specifically, the limiting means 400 is a blocking structure located at the sidewall 110 of the housing 100 attached to the cover 200. The blocking structure is located at a end of the cover 200 connected to the housing 100, such that the end of the cover 200 connected to the housing is stopped by the blocking structure when the cover 200 rotates to a certain angle, thereby preventing the cover 200 from further rotating.

In the illustrated embodiment, the maximum rotating angle ranges from 15 degrees to 75 degrees. If the maximum rotating angle is too small, the finger 22 to be measured may not able to reach a best measuring area between the cover 200 and the housing 100, or the cover 200 may press the finger 22 so hard to affect the measurement accuracy. If the maximum rotating angle is too large, the cover 200 may be detached from the finger 22 to be measured, thus resulting that the light emitting unit 312 is not aligned with the light receiving unit 314 during the measuring and the measuring result may not be obtained. Preferably, the maximum rotating angle is 45 degrees.

The restoring means 500 is configured to attach the cover 200 to the sidewall 110 of the housing 100. When the finger 22 to be measured is positioned between the cover 200 and the housing 100, the restoring means 500 can provide a resilience force to ensure the cover 200 presses against the finger 22, so as to reduce the gap between the finger 22 and the light emitting unit 312 and the light receiving unit 314, thereby increasing the measurement stability and accuracy. When the finger 22 is taken out, the cover 200 can be automatically attached to the sidewall 110 due to the restoring force of the restoring means 500, such that the light emitting unit 312 and the light receiving unit 314 can be well protected, and the cover 200 is not susceptible to accidental damage by external force, and a appearance is ensured.

In the illustrated embodiment, the restoring means 500 can be a magnetic mechanism, which includes two magnetic elements 510. The two magnetic elements 510 are located at a side of the cover 200 attached to the housing 100 and the sidewall of the housing 100 attached to the cover 200, respectively. Since the two magnetic elements 510 are located close to the connection between the cover 200 and the housing 100, they can be attracted to each other. It is to be understood that, in alternative embodiments, the magnetic mechanism can also includes a magnetic element and a metal sheet. The magnetic element is located at a side of the cover 200 attached to the housing 100, while the metal sheet is located at the sidewall 110 of the housing 100 attached to the cover 200. Since the magnetic element and the metal sheet are located close to the connection between the cover 200 and the housing 100, they can be attracted to each other. Alternatively, the metal sheet can be located at the side of the cover 200 attached to the housing 100, while the magnetic element is located at the sidewall 110 of the housing 100 attached to the cover 200.

In alternative embodiments, the restoring means 500 can be a torsion spring coiled on the rotating shaft 210.

In addition, for the convenience of inserting and lifting up the cover 200 attached to the housing 100 by the finger, a finger inserting recess 220 is provided between an end of the cover 200 away from the housing 100 and the sidewall 110.

Referring to FIG. 5, when using the handheld multi-parameter measuring instrument 10 to measure the blood oxygen saturation, one hand 20 of the user can hold the first surface 120 and the second surface 130 of the housing 100, and the finger 22 of the hand 20 can be place between the cover 200 and the housing 100. The signal processing unit 320 controls the light emitting unit 312 to emit the red light and the infrared light alternately, which go through the finger 22 or are reflected by the finger 22, and then transmitted to the light receiving unit 314. The signal processing unit 320 then calculates the oxygen saturation based on a signal received by the light receiving unit 314.

In the forgoing handheld multi-parameter measuring instrument 10, the cover 200 is disposed on the sidewall 110 of the housing 100, and the blood oxygen transducer 310 is integrated on the housing 100, therefore there is no need to employ cable, connector or the like, the instrument 10 has the features of easy to use, easy to maintain, low cost, high accuracy, and good resistance to ambient light interference.

When the light emitting unit 312 and the light receiving unit 314 are located at the same side, the cover 200 can effectively prevent the interference of ambient light, thereby enhancing the accuracy and repeatability of blood oxygen transducer 310. The cover 200 can also protect the light emitting unit 312 and the light receiving unit 314 from contamination and abrasion, which can affect the light transmittance, thereby further enhancing the accuracy and repeatability of blood oxygen transducer 310.

When the light emitting unit 312 and the light receiving unit 314 are located at opposite sides, the handheld multi-parameter measuring instrument 10 can have a better measuring accuracy comparing to the reflective-type blood oxygen transducer 310. The handheld multi-parameter measurement instrument 10 is easy to use, easy to maintain, very suitable for non-professional home self-test use. In addition, since the cover 200 is disposed on the sidewall 110 of the housing 100, there will be more space in the housing 100 for integrating other sensors.

Furthermore, during the measuring of blood oxygen saturation using the handheld multi-parameter measurement instrument 10, the user can hold the instrument 10 by hand 20, and the cover 200 presses the finger 22 to measure the blood oxygen saturation, thus the case of displacement or loss of blood oxygen measuring device may not occur. Compared to the conventional wearable oximeter, there is no need for the finger 22 to be measured to bear the weight of the device, and it is not necessary to provide a great clamping force (which can affect the smooth flow of local blood flow of the finger thus affecting the measurement) to maintain the device from falling off, as a result, the handheld multi-parameter measuring instrument 10 can effectively improve the comfort and improve the measurement accuracy of the measurements. Moreover, the user can walk freely during the measuring, thus it is convenient. Still further, when using the handheld multi-parameter measurement instrument 10 to measure the blood oxygen saturation by one hand, the other hand of the user is idle, thus it is convenient for the user to detect other physiological parameters simultaneously, therefore the handheld multi-parameter measurement instrument 10 has a functional diversity over conventional oximeter with one function of measuring blood oxygen saturation.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. A handheld multi-parameter measuring instrument, comprising:
    a housing having a sidewall and opposed first and second surfaces, the sidewall, the first surface and the second surface cooperatively forming a cavity;
    a cover attached to the sidewall and rotatably connected to the housing, a finger being capable of being received between the cover and the sidewall of the housing attached to the cover; and
    a blood oxygen measuring device comprising a blood oxygen transducer and a signal processing unit, the blood oxygen transducer comprising a light emitting unit and a light receiving unit; the light emitting unit being configured to emit red light and infrared light alternately; the light receiving unit being configured to receive the red light and the infrared light emitted from the light emitting unit; wherein the signal processing unit is received in the cavity of the housing and controls the light emitting unit to emit the red light and the infrared light alternately; the signal processing unit is further configured to calculate oxygen saturation based on a signal received by the light receiving unit;
    an electrocardiogram (ECG) sensor, comprising: a first ECG electrode located on the first surface and adapted to engage a surface of a thumb of a right hand while the right hand is supporting the instrument and the finger is received between the cover and the sidewall, and a second ECG sensor located on the sidewall and adapted to engage a palm of a left hand while the right hand is supporting the instrument;
    wherein (a) the light emitting unit is located at a side of the cover attached to the housing, and the light receiving unit is located at the sidewall of the housing attached to the cover; or (b) the light emitting unit is located at the sidewall facing the cover, and the light receiving unit is located at a side of the cover facing the housing; or (c) the light emitting unit and the light receiving unit are both located at the sidewall facing the cover;
    wherein the cover has an open and a closed position, the closed position being adapted to prevent entry of a finger into the instrument, and the open position being adapted to receive the finger such that the forward end of the finger is completely accessible to an environment external to the instrument while the blood oxygen measuring device measures blood oxygen.

2. The handheld multi-parameter measuring instrument according to claim 1, wherein the blood oxygen measuring device further comprises:
    an optoelectronic interface unit, by which the light emitting unit and the light receiving unit are electrically coupled to the signal processing unit;
    a memory unit received in the cavity and electrically coupled to the signal processing unit, the memory unit being configured to store the oxygen saturation calculated by the signal processing unit; and
    a display unit located at the housing, the display unit being electrically coupled to the signal processing unit and configured to display the oxygen saturation calculated by the signal processing unit.

3. The handheld multi-parameter measuring instrument according to claim 1, wherein the signal processing unit is further configured to calculate at least one of pulse rate, perfusion strength, and pulse waveform based on the signal received by the light receiving unit.

4. The handheld multi-parameter measuring instrument according to claim 1, wherein the cover and the sidewall of the housing attached to the cover form a buffer chamber therebetween.

5. The handheld multi-parameter measuring instrument according to claim 1, wherein the housing has a rectangular shape, when a right hand of a user holds the first surface and the second surface, the first surface faces the user, the cover is located at a upper right of the housing, and the cover is attached to a sidewall at the corner of the housing or a sidewall at the top of the housing.

6. The handheld multi-parameter measuring instrument according to claim 5, wherein the cover and the sidewall of the housing attached to the cover form a buffer chamber therebetween, and the buffer chamber is formed by depressing inward of sidewall of the housing attached to the cover.

7. The handheld multi-parameter measuring instrument according to claim 6, wherein the cover is attached to the sidewall located at the corner of the housing, and the cover and the sidewall of the housing attached to the cover form the buffer chamber therebetween; the cover is a curved plate, the sidewall of the housing attached to the cover has an arcuate shape, the buffer chamber is formed by the cover and the sidewall of the housing attached to the cover cooperatively.

8. The handheld multi-parameter measuring instrument according to claim 7, wherein a curvature of the outer surface of the cover is the same as a curvature direction of the sidewall of the housing attached to the cover; a bending direction of the outer surface of the cover is the same as a bending direction of the sidewall of the housing attached to the cover, and a center of a circle of the outer surface of the cover is located inside the housing.

9. The handheld multi-parameter measuring instrument according to claim 1, further comprising a block located at the housing configured to limit a maximum rotating angle of the cover with respect to the housing, the maximum rotating angle ranging from 15 degrees to 75 degrees.

10. The handheld multi-parameter measuring instrument according to claim 9, wherein the block is located at an end of the cover connected to the housing, such that the end of the cover connected to the housing is stopped by the block when the cover rotates to a certain angle, thereby preventing the cover from further rotating.

11. The handheld multi-parameter measuring instrument according to claim 1, further comprising restoring means comprising a spring or at least a first magnet configured to attach the cover to the sidewall of the housing.

12. The handheld multi-parameter measuring instrument according to claim 11, wherein the restoring means comprises:
 (a) the first magnet located at a side of the cover attached to the housing and a second magnet located at the sidewall of the housing attached to the cover, the first and second magnets being attracted to each other;
 or (b) the first magnet and a metal sheet, one of the first magnet and the metal sheet being located at a side of the cover attached to the housing, and the other of the first magnet and the metal sheet being located at the sidewall of the housing attached to the cover, wherein the first magnet is attracted to the metal sheet.

13. The handheld multi-parameter measuring instrument according to claim 11, wherein the cover is rotatably connected to the housing via a rotating shaft, the restoring means is a torsion spring coiled on the rotating shaft.

14. The handheld multi-parameter measuring instrument according to claim 1, wherein a finger inserting recess is provided between an end of the cover and the sidewall, wherein the cover attached to the housing is adapted to open in response to insertion of the finger into the finger inserting recess.

15. The instrument of claim 1, wherein the first electrode has a circle cross section.

* * * * *